United States Patent
Rustad et al.

(10) Patent No.: US 10,711,594 B2
(45) Date of Patent: Jul. 14, 2020

(54) METHOD AND SYSTEM FOR DETERMINING FLOW RATE OF WATER IN A GAS PRODUCTION SYSTEM BY INCORPORATING CHARACTERISTICS OF WATER

(71) Applicant: ONESUBSEA IP UK LIMITED, London (GB)

(72) Inventors: Rolf Rustad, Bergen (NO); Andrew Charles Baker, Bergen (NO); Alexandre Lupeau, Bergen (NO)

(73) Assignee: ONESUBSEA IP UK LIMITED, London (GB)

( * ) Notice: Subject to any disclaimer, the term of this patent is extended or adjusted under 35 U.S.C. 154(b) by 109 days.

(21) Appl. No.: 15/767,150

(22) PCT Filed: Oct. 21, 2016

(86) PCT No.: PCT/EP2016/075417
§ 371 (c)(1),
(2) Date: Apr. 10, 2018

(87) PCT Pub. No.: WO2017/068144
PCT Pub. Date: Apr. 27, 2017

(65) Prior Publication Data
US 2018/0298748 A1 Oct. 18, 2018

Related U.S. Application Data

(60) Provisional application No. 62/245,556, filed on Oct. 23, 2015, provisional application No. 62/355,514, (Continued)

(51) Int. Cl.
*E21B 47/10* (2012.01)
*G01F 1/44* (2006.01)
(Continued)

(52) U.S. Cl.
CPC .............. *E21B 47/10* (2013.01); *E21B 37/06* (2013.01); *G01F 1/44* (2013.01); *G01F 1/74* (2013.01);
(Continued)

(58) Field of Classification Search
None
See application file for complete search history.

(56) References Cited

U.S. PATENT DOCUMENTS

| 4,727,489 A | * | 2/1988 | Frazier ................... E21B 43/34 166/265 |
| 6,292,756 B1 | | 9/2001 | Lievois et al. |
| 6,831,470 B2 | | 12/2004 | Xie et al. |

FOREIGN PATENT DOCUMENTS

| GB | 2376074 A | 12/2002 |
| GB | 2426579 A | 11/2006 |
| GB | 2482984 A | 2/2012 |

OTHER PUBLICATIONS

International Search Report and Written Opinion issued in International Patent Application No. PCT/EP2016/075417 dated Jan. 23, 2017; 11 pages.

* cited by examiner

*Primary Examiner* — Harshad R Patel
(74) *Attorney, Agent, or Firm* — Helene Raybaud

(57) ABSTRACT

A method is provided for determining the flow rate of formation water and/or the total rate of produced water in a gas well. More particularly, a method and system is provided to determine the flow rates of gas, condensate, and water in gas production using a flowmeter.

22 Claims, 6 Drawing Sheets

Related U.S. Application Data filed on Jun. 28, 2016, provisional application No. 62/384,771, filed on Sep. 8, 2016.

(51) Int. Cl.
*E21B 37/06* (2006.01)
*G01F 1/74* (2006.01)
*G01N 27/06* (2006.01)
*G01N 33/24* (2006.01)
*G01N 33/28* (2006.01)

(52) U.S. Cl.
CPC ........... *G01N 27/06* (2013.01); *G01N 33/241* (2013.01); *G01N 33/2847* (2013.01)

METHOD AND SYSTEM FOR DETERMINING FLOW RATE OF WATER IN A GAS PRODUCTION SYSTEM BY INCORPORATING CHARACTERISTICS OF WATER

REFERENCE TO RELATED APPLICATIONS

This patent application claims the benefit of and incorporates by reference each of the following provisional applications:
U.S. Prov. Ser. No. 62/245,556 filed Oct. 23, 2015;
U.S. Prov. Ser. No. 62/355,514 filed Jun. 28, 2016; and
U.S. Prov. Ser. No. 62/384,771 filed Sep. 8, 2016.

TECHNICAL FIELD

The present disclosure relates to a method and system to determine the production rate of fluids in a gas well. More particularly, the present disclosure relates to a method and system to determine the production rate of formation water and/or the total rate of produced water in a gas well by determining the salinity of liquid water in the well effluent, and to use this information in combination with other data to obtain a corrected gas rate. Corrected liquid rates may be derived from the corrected gas rate.

BACKGROUND

Water and hydrate management is a known challenge in subsea gas developments. Hydrates are formations of ice and gas that may form due to high pressures and low temperatures in hydrocarbon extraction environments. These hydrates may then clog the production systems, leading to hazardous conditions. Many subsea gas wells produce no to very little formation water at start-up. The gas in the reservoir is (nearly) always saturated with water vapor. At the wellhead or other location within the gas production system, some of the water vapor may have condensed and may be present as condensed or de-ionized water. If so, there will still be water in the vapor phase in the gas at the wellhead and throughout the production system, and thus further condensation of water may occur downstream of the wellhead.

Gas reservoirs might contain salty, interstitial water in the source rock, or may be connected to aquifers containing salty formation water. However, it may be desirable for a well operator to continue producing gas from a well even after that well has started to produce such formation water. The volumetric fraction of formation water in the production fluid is usually very small, for example less than about 1% of the total volume, making it difficult to accurately measure the production rate of formation water. To complicate things further, the formation water and the condensed water might mix as water is condensing out of the gas vapor phase in the wellbore, at the wellhead, and/or further downstream in the production system.

In some installations, a measurement device such as a multiphase or wet gas meter may be located at or near the wellhead to measure the production rates of gas, gas condensate, and water. The total water fraction being small, the associated measurement uncertainty is correspondingly large to the point of significantly impairing the accuracy of such measurement. For example, a wet gas meter may have a water volume fraction measurement uncertainty of 0.1%, while the actual liquid water volume fraction might be 0.05% (500 ppm).

SUMMARY

This summary is provided to introduce a selection of concepts that are further described below in the detailed description. This summary is not intended to identify key or essential features of the claimed subject matter, nor is it intended to be used as an aid in determining or limiting the scope of the claimed subject matter as set forth in the claims.

According to some embodiments of the disclosure, a method is described to determine water flow rates in a gas production system from a gas well penetrating a subterranean formation. The method includes: determining a flow rate of gas flowing past a measurement location within the gas production system; calculating a flow rate of condensed liquid water flowing past the measurement location that has condensed from water vapor originating from the subterranean formation based at least in part on the determined gas flow rate; measuring characteristics of water flowing past the measurement location from which a determination can be made as to what portion of liquid water flowing past the measurement location that originated as water produced as a liquid by the formation; and combining the measured characteristics and knowledge about water residing in the formation with the calculated flow rate of condensed liquid water to derive a flow rate of water produced as a liquid by the formation. According to some embodiments, the various measurements may also be made at different locations in a production system when the pressure and temperature at each location is known or measured.

According to some embodiments, salinity of total liquid water flowing past the measurement location is determined based at least in part on the measured characteristics of water, and the knowledge about the water includes knowledge about salinity of water residing in the formation. The measured characteristics, which can include for example conductivity can be measured in situ using a probe located within gas production system, or by taking and analyzing samples of liquid water.

According to some embodiments, the calculation of condensed liquid water flow rate is also based on a flow rate of water vapor expected to have condensed from vapor given pressure and temperature conditions in the formation and at the measurement location. The calculation of condensed liquid water flow rate may be used to calculate a mass ratio of condensed liquid water to gas at the measurement location, or the mass ratio of condensed liquid water to gas may be calculated by difference means, like an equation of state model.

According to some embodiments, the calculation of condensed oil flow rate is also based on a flow rate of oil expected to have condensed from the hydrocarbon gas given pressure and temperature conditions in the formation and at the measurement location. The calculation of condensed oil flow rate may be used to calculate a mass ratio of condensed oil to gas at the measurement location, or the mass ratio of condensed oil to gas may be calculated by difference means, like an equation of state model.

According to some embodiments, the gas flow rate determination includes: calculating a flow rate using differential pressure measurements; and adjusting the flow rate to account for the presence of condensed water and condensed oil entrained in the gas. In some cases the adjustment can be based in part on a calculated Lockhart-Martinelli parameter.

According to some embodiments, a system is described that is configured to determine water flow rates in a gas production system from a gas well penetrating a subterranean formation. The system can include: a flow meter positioned at a measurement location within the gas production system, the flow meter configured to measure a flow rate of gas; a processing system configured to calculate a flow rate of condensed liquid water that has condensed from vapor originating from the subterranean formation; and a measurement device configured to measure electromagnetic properties of the produced fluid from which salinity of total liquid water flowing past the device can be determined, the processing system further configured to combine the determined salinity of the total liquid water and knowledge about the salinity of water residing in the formation with the calculated flow rate of condensed liquid water to derive a flow rate of water produced as a liquid by the formation. According to some embodiments the flow meter can be a wet gas flow meter, a differential pressure device, or an ultrasonic flow meter.

According to some embodiments, a plurality of sensors are connected to a control system that is configured to calculate injection rates of chemicals within the gas production system based on at least one of the flow rates of water produced as a liquid by the formation or a total flow rate of produced water. The control system might be connected to a choke valve and/or a chemical injection metering valve, and controls the choke valve and/or chemical injection metering valve based on at least one of the flow rate of water produced as a liquid by the formation or the total flow rate of produced water.

In a case where the gas well is a subsea gas well and the measurement location is a subsea location, one or more of the sensors can be installed in a subsea module that is retrievably connected to the gas production system. The module can include the control system, a chemical injection metering valve, and/or a choke valve. In some cases, the module is located within the gas production system at a well head, in a jumper, a pipeline end termination (PLET), a pipeline end manifold (PLEM), a high-integrity pressure protection system (HIPPS) or a manifold.

BRIEF DESCRIPTION OF THE DRAWINGS

The subject disclosure is further described in the following detailed description, and the accompanying drawings and schematics of non-limiting embodiments of the subject disclosure. The features depicted in the figures are not necessarily shown to scale. Certain features of the embodiments may be shown exaggerated in scale or in somewhat schematic form, and some details of elements may not be shown in the interest of clarity and conciseness.

DETAILED DESCRIPTION

The particulars shown herein are for purposes of illustrative discussion of the embodiments of the present disclosure only. In this regard, no attempt is made to show structural details of the present disclosure in more detail than is necessary for the fundamental understanding of the present disclosure, the description taken with the drawings making apparent to those skilled in the art how the several forms of the present disclosure may be embodied in practice. As used herein the term "well" refers to a subsea, offshore, or onshore well.

According to some embodiments, methods and systems are described for determining the flow rates of formation water and/or the total rates of produced water in a gas well by determining the salinity of the liquid water in the well effluent. According to some embodiments, the conductivity of the liquid water in the production system is used to determine salinity. The measurement might be performed at the wellhead or some other location downstream from the wellbore. This measurement may be performed with a conductivity probe located at the wellhead, in the Christmas tree, in the manifold, or in some other convenient location in a subsea production system. Other sensors or methods may also be used to obtain the salinity of the water.

Figure 1:
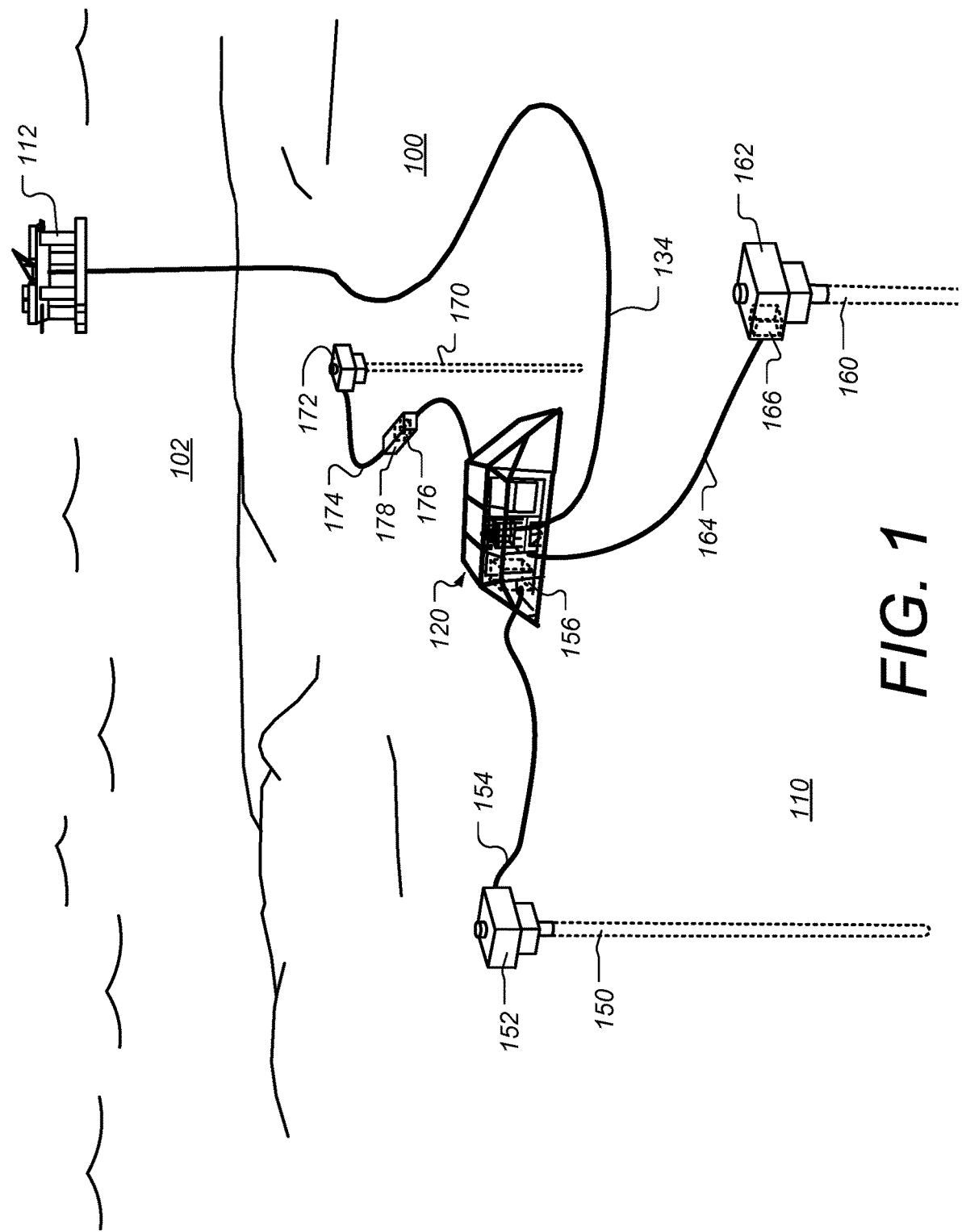
FIG. 1 is a diagram illustrating a subsea production system where a method and system for determining water production rates in gas wells could be deployed, according to some embodiments.

FIG. 1 is a diagram illustrating a subsea production system where a method and system for determining water production rates in gas wells could be deployed, according to some embodiments. On sea floor 100 a subsea station 120 is shown which is located in the vicinity of wellheads 152, 162 and 172 for wells 150, 160 and 170 respectively. Wells 150, 160 and 170 are being used in the recovery of hydrocarbon gas from a subterranean rock formation 110. Each of the wellheads 152, 162 and 172 include an assembly of valves, spools and fittings that make up a Christmas tree, for the purpose of controlling the flow of fluids during production. According to some embodiments, measuring systems that can include either a flow rate measurement system and/or salinity measurement system could be located at various locations in the subsea production system shown in FIG. 1. For example, measurement systems could be included with the Christmas tree at one or more of the wellhead locations, such as measuring system 166 at wellhead 162. The gas produced from the wellheads 152, 162 and 172 flow through flowlines 154, 164 and 174 respectively towards station 120. According to some embodiments, measuring systems can be included along one or more of the flowlines. For example, measurement system 176 is shown installed in a high-integrity pressure protection system (HIPPS) 178 on flowline 174. Station 120, which includes a manifold, could also include one or more measurement systems such as measurement system 156 installed at an inlet of the manifold. Locating the measurement system upstream of the confluence of the manifold has a benefit of providing capability to determine flow rates, including formation water flow rates, for each of the individual wells. According to some other embodiments, however, measurement systems can also be located downstream of a manifold such as along umbilical and flowline 134 or some other location. The umbilical and flowline in this case is being run to and from a platform 112 through seawater 102, along sea floor 100 to station 120. In other cases, the flowline and umbilical may be run from some other surface facility such as a floating production, storage and offloading unit (FPSO), or a shore-based facility. Other equipment such as other wells, other subsea stations, other umbilicals, and flowlines may be present as well, although not shown in this diagram for simplicity.

In subsea gas well developments, an example of which is shown in FIG. 1, water and hydrate management can be a concern. The gas in a subsea reservoir, such as reservoir 110, can be saturated with water in the vapor phase. Gas wells, such as wells 150, 160 and 170, will therefore likely produce water along with the gas when the gas comes out of the reservoir formation. At reservoir conditions this water is in the vapor phase, but as the pressure and temperature are reduced while the gas travels up the wellbore and through the subsea production system, some of the water vapor may condense. In addition, a gas reservoir might contain salty formation water in the source rock and there might also be one or more aquifers in the subterranean formation that may be in fluid communication with the gas reservoir. New gas wells will usually be constructed to avoid the production of formation water, at least initially. However, formation water from the source rock or from aquifers might encroach into the gas well and add to the water initially present in vapor phase. Although the gas wells in FIG. 1 are shown as subsea wells, the techniques described herein are also applicable to surface and transition zone gas wells and as such all references in this description to subsea gas wells are understood to also apply to gas wells on the surface and to gas wells in transition zones.

According to some embodiments, a method is described that includes combining knowledge of reservoir conditions with measurements of the gas flow rate and measurements relating to the salinity of liquid water. The measurements of gas flow rate and or salinity-relating measurements can be made by one or more measurement systems such as systems 156, 166 and/or 176 shown in FIG. 1. The associated water produced from the formation may be calculated by applying the steps/formula as further described below wherein:
  a. m denotes metering conditions, e.g. the pressure and temperature at which the gas rate measurement is made;
  b. r denotes reservoir conditions, e.g. the pressure and temperature at which the gas enters the wellbore;
  c. q denotes volumetric flow rate;
  d. Q denotes mass flow rate;
  e. g denotes gas; and
  f. w denotes water.

For example, Pm is the pressure at metering conditions, while $q_{g,r}$ is the volumetric flow rate of gas at reservoir conditions.

According to some embodiments, a method is described for determining the production rate of formation water by: measuring the flow rate of gas $q_{g,m}$, the temperature $T_m$, and the pressure $P_m$ at a suitable location, for instance near the well head; converting the gas flow rate to reservoir conditions $T_r$ and $P_r$ through suitable known pressure-volume-temperature (PVT) calculations to obtain the reservoir gas flow rate $q_{g,r}$; and calculating the total flow rate of water associated with the gas and in the vapor phase using:

$$q_{w,vap,r} = \frac{P_{water}^{Sat.}(T_r)}{P_r} q_{g,r} \quad [1]$$

where: $P_{water}^{Sat.}(T_r)$ is the saturation pressure of water at reservoir temperature; and $P_r$ is the reservoir pressure.

According to some other embodiments, an Equation of State and/or other known equations may be used to calculate the flow rate of water associated with the gas in the vapor phase $q_{w,vap,r}$.

According to some embodiments, methods are described to determine the production rate of formation water, which may include calculating a partition of $q_{w,vap,r}$ between the vapor phase and the liquid phase at metering conditions. At metering conditions, the flow rate of water in the vapor phase can be identified by $$q_{w,vap,m} = \frac{P_{water}^{Sat.}(T_m)}{P_m} q_{g,m} \quad [2]$$

The mass rate of water condensed from the vapor phase to the liquid phase at measurement conditions is then $$Q_{w,cond,m} = Q_{w,vap,r} - Q_{w,vap,m} \quad [3]$$
$$= \rho_{w,vap,r} \frac{P_{water}^{Sat.}(T_r)}{P_r} q_{g,r} - \rho_{w,vap,m} \frac{P_{water}^{Sat.}(T_m)}{P_m} q_{g,m}$$

In other embodiments of the disclosure, one may use an Equation of State to calculate the partition of $q_{w,vap,r}$ between the vapor phase and the liquid phase at metering conditions.

In other embodiments of the disclosure, one may use different known equations to achieve the outcome of the disclosed method.

In some embodiments, the method of the present disclosure may include obtaining the salinity of the liquid water at metering conditions. In an embodiment, this may be achieved by subsea sampling and subsequent analysis of this water. In another embodiment, such measurement may be obtained in real time and/or on a continuous basis. This may be achieved by measuring the electromagnetic properties, e.g. the permittivity and/or conductivity, or complex permittivity, of the mixture of condensed water and formation water, or a mixture of liquid water and other fluids in the well effluent, and calculating the water salinity from these measurements. This is described for example in U.S. Pat. No. 6,831,470, entitled "Methods and apparatus for estimating on-line water conductivity of multiphase mixtures," which is incorporated herein in its entirety.

The method of the present disclosure may include calculating the ratio of formation water to condensed water at metering conditions. In an embodiment, one may assume the salinity of the formation water is known, for instance from a water sample obtained during exploration and appraisal. Otherwise, the salinity of the formation water may also be obtained through modeling of the formation characteristics. The below equation might be used wherein:
  a. F denotes formation water;
  b. $S_F$ is the salinity of the formation water; and
  c. $S_m$ is the salinity of the liquid water at measurement conditions.

The formation water mass flow rate $Q_{w,F}$ is:

$$Q_{w,F} = \frac{S_m}{(S_F - S_m)} Q_{w,cond,m} \quad [4]$$

The total water mass flow rate is then:

$$Q_{w,total} = \rho_{w,vap,r} q_{w,vap,r} + Q_{w,F} \quad [5]$$

Figure 2:
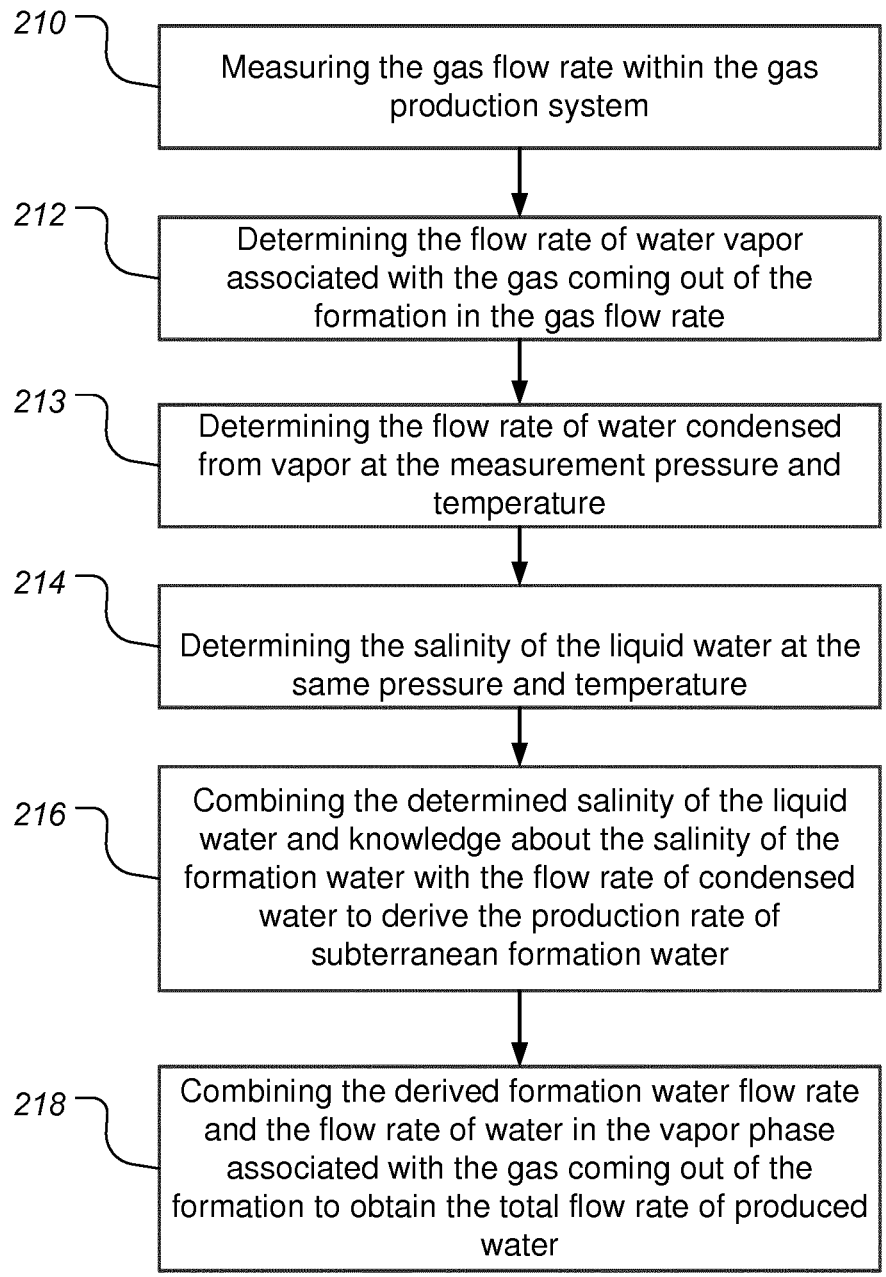
FIG. 2 is a flow chart illustrating some aspects of determining the production rate of formation water in a gas well, according to some embodiments.

FIG. 2 is a flow chart illustrating some aspects of determining production rate of formation water in a gas well, according to some embodiments. In block 210, the gas flow rate is measured at a location of the gas production system. In block 212, the flow rate of water vapor in the gas coming out of the formation is determined. In block 213, the flow rate of liquid water being condensed out of vapor coming out of the formation is determined at a measurement location in the gas production system. In block 214, a property of liquid water, of the mixture of formation liquid water and condensed water, or of a mixture of liquid water and other fluids in the well effluent, are measured at a measurement location. From one or more of these measurements, the salinity of this liquid water it determined. According to some other embodiments, the salinity of the liquid water can be obtained alternatively through sampling and analysis. In block 216, the derived or measured salinity, knowledge about the salinity of the formation water and the flow rate of condensed water are combined to derive the formation water flow rate. In block 218, the derived formation water flow rate and the flow rate of water coming out of the formation in the vapor phase associated with the gas are combined to obtain the total production rate of formation water.

Figure 3:
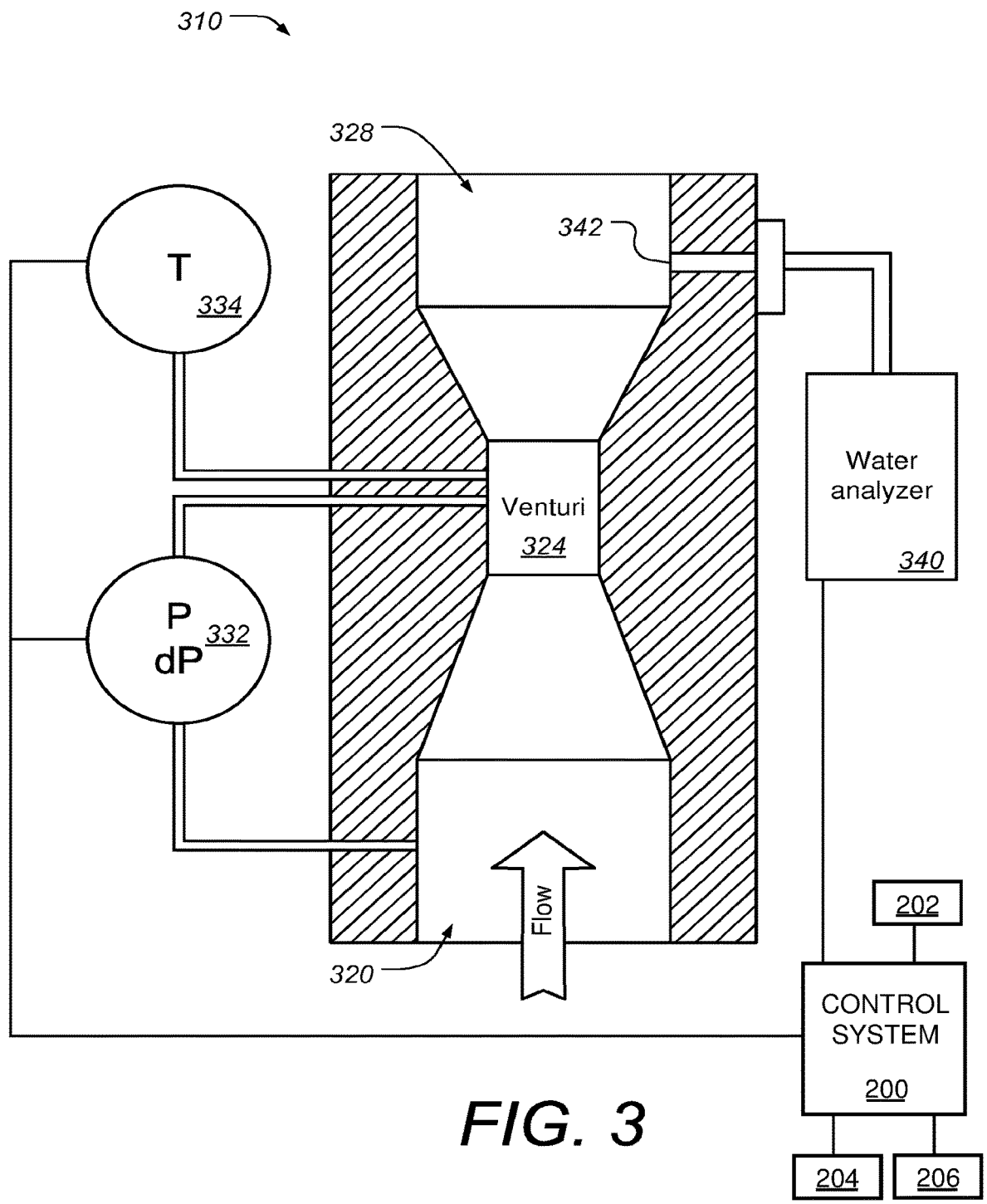
FIG. 3 is a diagram illustrating a measurement system that could be used in connection with some embodiments.

FIG. 3 is a diagram illustrating a measurement system that could be used in connection with some embodiments. Measurement system 310 includes a differential pressure device that is a Venturi tube in this example. Inlet 320 leads to Venturi throat 324 followed by outlet 328. The Venturi tube is used to provide a differential pressure (dP) measurement in a pipe section of a gas production installation. For example, the measurement system 310 could be installed in various locations such as measurement systems 156, 166 and 176 in FIG. 1. Differential pressure dP is measured between inlet 320 and throat 324 using pressure sensor(s) 332. According to some embodiments, pressure P and temperature T are also measured at the same location or close by, for example using sensors 332 and 334 respectively. Although the example in FIG. 3 measures differential pressure using a Venturi tube, other types of differential pressure devices could be used such as a Venturi nozzle, a V-cone, or an orifice plate. According to some embodiments, a water analyzer 340 is also provided which can measure water properties at location 242. According to some embodiments, analyzer 340 is a water analysis sensor such as OneSubsea AquaWatcher™ Water Analysis Sensor that can detect the presence of water in multiphase and wet gas flows, and determine the salinity of that water. According to some embodiments a different type of flow meter can be used, such as an ultrasonic flow meter.

Figure 4A:
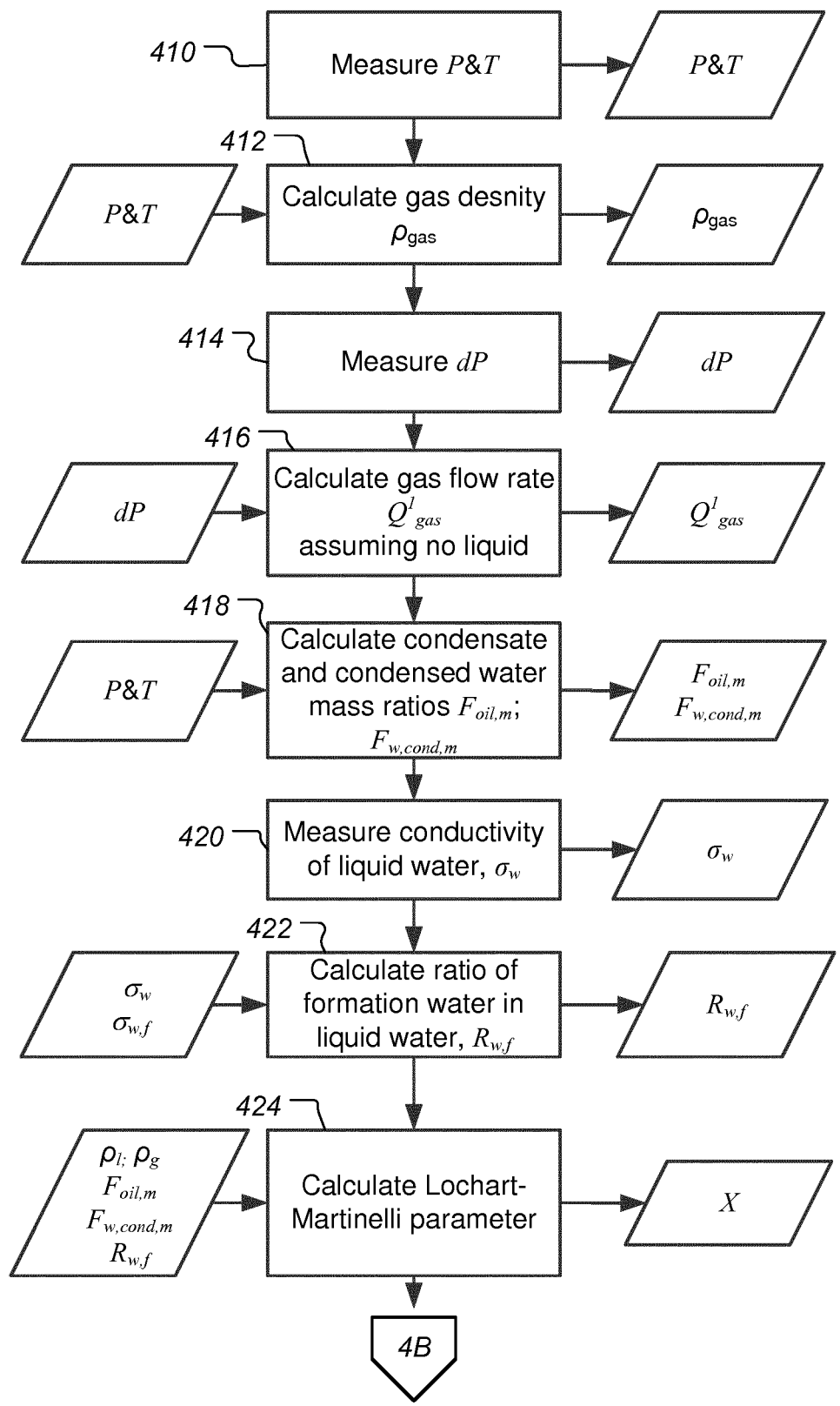
FIGS. 4A and 4B are a flow chart illustrating further aspects of determining formation water flow rate and other fluid flow rates in gas wells, according to some embodiments.
Figure 4B:
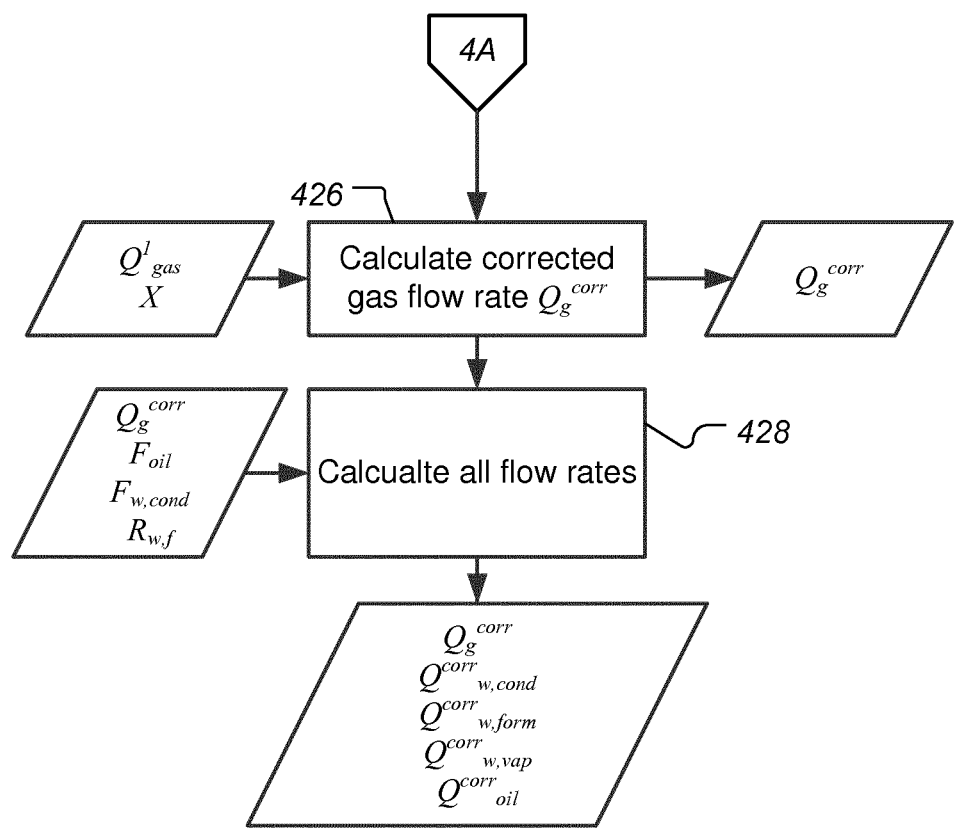

FIGS. 4A and 4B are a flow chart illustrating further aspects of determining flow rates of formation water and other fluids in gas wells, according to some embodiments. In block 410, the pressure and temperature are measured at a measuring location. In block 412, the gas density $\rho_{gas}$ at the measured pressure and temperature is calculated. This can be done if the composition of the gas is known, for instance, or the properties of the gas can be measured if a sample is available. In block 414, the differential pressure, dP, is also measured at the measurement location, for instance by use of sensor 332 in FIG. 3. In block 416, a first gas mass flow rate $Q_{gas}^1$ is calculated using, for example, the Bernoulli equation:

$$Q_{gas}^1 = kC_d\sqrt{\rho_g dP}$$

where k is a constant, and $C_d$ is the discharge coefficient.

In block 418, various methods may be employed to calculate the mass ratios of hydrocarbon condensate $F_{oil,m}$ and condensed water $F_{w,cond,m}$ with respect to gas at the same conditions. Known methods are described in literature, and will not be discussed in detail here. The mass ratios are defined by the following equations, where all values are at measurement conditions:

$$F_{oil,m} = \frac{Q_{oil,m}}{Q_{gas,m}}$$

$$F_{w,cond,m} = \frac{Q_{w,cond,m}}{Q_{gas,m}}$$

For the purpose of the following description, we will assume that the ratio of hydrocarbon condensate $F_{oil,m}$ is known from analysis of a fluid sample, and that the ratio of liquid condensed water $F_{w,cond,m}$ is calculated from a measurement of the downhole conditions and the saturation pressure of water at the meter conditions $P_m$ and $T_m$. An equation of state model can be used to provide the water in vapor. According to some embodiments, the calculation of the gas density discussed above may include a calculation of the water in vapor.

According to the example of FIG. 4A, in block 422 data is measured relating to the ratio of formation water to liquid water defined as:

$$R_{w,f} = \frac{Q_{w,f}}{Q_{w,l,m}}$$

where $Q_{w,f}$ is the mass flowrate of formation water and $Q_{w,l,m}$ is the mass flow rate of liquid water at metering conditions:

$$Q_{w,l,m} = Q_{w,cond,m} + Q_{w,f}$$

$R_{w,f}$ may be provided by measuring the conductivity and permittivity of the fluid mixture, and deriving from there the conductivity and then the salinity of the water. A water analysis tool such as the OneSubsea Aqua Watcher™ Water Analysis Sensor can be used to perform this measurement, but other sensors or combinations of sensors may also be employed. $R_{w,f}$ may also be determined by analyzing a fluid sample from the well stream. Assuming that the salinity of the formation water is known, it is now possible to calculate the ratio of formation water to liquid water $R_{w,f}$:

$$R_{w,f} = \frac{S_w}{S_{w,f}}$$

where $S_w$ is the measured or estimated salinity of the water phase at measurement conditions, and $S_{w,f}$ is the salinity of the formation water. Other fluids containing salt may be injected into the flowstream upstream of measurement. In this case these need to be accounted for.

Alternatively, the ratio may be estimated directly from the conductivities. To a first approximation this can be calculated by:

$$R_{w,f} = \frac{\sigma_w}{\sigma_{w,f}}$$

where $\sigma_w$ is the conductivity (e.g. measured in block 420) of the water phase at measurement conditions, and $\sigma_{w,f}$ is the conductivity of the formation water. More complex models may be employed. If other conductive fluids are present, such as chemicals injected upstream of measurement, these need to be corrected for.

The uncorrected mass rates of condensate (oil), condensed water, and formation water, and the total liquid mass flow are calculated as follows, where the densities are calculated at measurement conditions.

$$Q_{oil}^1 = F_{oil,m} * Q_{gas}^1$$

$$Q_{w,cond}^1 = F_{w,cond,m} * Q_{gas}^1$$

$$Q_{w,f}^1 = \frac{R_{w,f}}{1 - R_{w,f}} * Q_{w,cond}^1$$

$$Q_{liq,tot}^1 = Q_{w,f}^1 + Q_{w,cond}^1 + Q_{oil}^1.$$

All these flow rates may be corrected later, once a corrected gas rate has been derived.

Many of the methods used to correct the over-reading of the gas rate are based on the Lockhart-Martinelli parameter. According to some embodiments, in block 424 the Lockhart-Martinelli parameter X is calculated, which at metering conditions can be expressed as:

$$X = \frac{Q_{l,m}}{Q_{g,m}} \sqrt{\frac{\rho_{g,m}}{\rho_{l,m}}}$$

We now substitute for $Q_{l,m}$ $$X = \frac{Q_{w,f}^1 + Q_{w,cond}^1 + Q_{oil}^1}{Q_{gas}^1} \sqrt{\frac{\rho_{g,m}}{\rho_{l,m}}}$$

$$= \frac{\left(\left(\frac{R_{w,f}}{1-R_{w,f}} + 1\right) F_{w,cond,m} + F_{oil,m}\right) Q_{gas}^1}{Q_{gas}^1} \sqrt{\frac{\rho_{g,m}}{\rho_{l,m}}}$$

$$= \left(\left(\frac{R_{w,f}}{1-R_{w,f}} + 1\right) F_{w,cond,m} + F_{oil,m}\right) \sqrt{\frac{\rho_{g,m}}{\rho_{l,m}}}$$

This expression is independent of the flow rates. It depends only on the calculated mass fractions and densities, and the salinity of the liquid water.

According to some embodiments of the disclosure, in step 426 the Lockhart-Martinelli parameter may be used to make a correction of the gas flow rate. The corrected estimate of the gas flow rate is $$Q_{gas}^{corr} Q_{gas}^1 * f(X)$$

where f(X) is a correction factor calculated from the Lockhart-Martinelli parameter. According to some embodiments, instead of using the Lockhart Martinelli parameter another method can be used to make the correction.

In block 428, the flow rates are calculated for the liquid rates, the water in vapor, and the total water produced:

$$Q_{oil}^{corr} = F_{oil,m} * Q_{gas}^{corr}$$

$$Q_{w,cond}^{corr} = F_{w,cond,m} * Q_{gas}^{corr}$$

$$Q_{w,f}^{corr} = \frac{R_{w,f}}{1 - R_{w,f}} * Q_{w,cond}^{corr}$$

$$Q_{w,liq,tot}^{corr} = Q_{w,f}^{corr} + Q_{w,cond}^{corr}.$$

In some embodiments, the same methodology may be applied to a combination of an ultrasonic gas flow meter and means to determine $R_{w,f}$, e.g. Aqua Watcher. The correction factor f(X) may in this case be different.

In some embodiments, the sensors (e.g., 332, 334, 340) used to obtain the measurements described may all be connected to a subsea or topside computer (such as in platform 112 in FIG. 1), or in a subsea control system (such as in station 120 in FIG. 1), hereafter referred to in common as a "control system", such as a control system 200 as illustrated in FIG. 3. The control system 200 may operate software designed to calculate injection rates of chemicals based on the information obtained through the methods here described, for instance.

The control system 200 may further be connected to a choke valve 202 and/or a chemical injection metering valve (CIMV) 204 or an injection control valve 206, and may act on one or several of these devices on the basis of information derived through the methods here described. Using the control system 200 and one or more of such valves 202, 204, and 206, information about total water flow rate and formation water flow rate may be used to regulate the injection rate of chemicals such as hydrate inhibitors, scale inhibitors, pH modifiers, corrosion inhibitors, and so on. It may further be useful for understanding the behavior and development of the reservoir, and or other applications to manage the gas well production.

Figure 5:
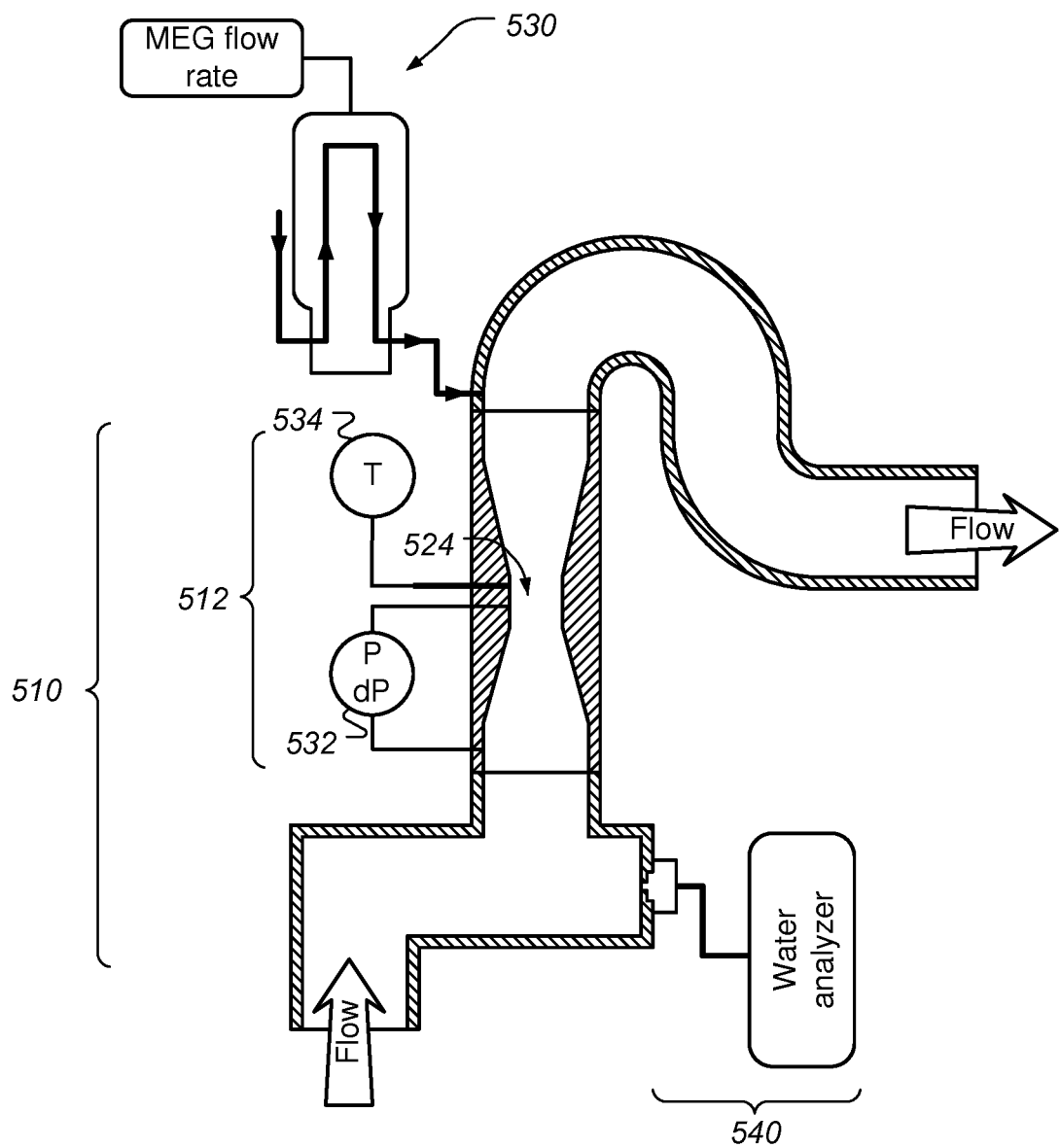
FIG. 5 is a diagram illustrating further aspects of a measurement system that can be used in connection with determining formation water and total water flow rates in gas wells, according to some embodiments.

FIG. 5 is a diagram illustrating further aspects of a measurement system that can be used in connection with determining formation water and total water flow rates in gas wells, according to some embodiments. In this example, the measurement system 510 is being used to measure pressure, pressure differential and temperature in a manner similar to that of measurement system 310 shown in FIG. 3. In particular at location 512, a Venturi tube 524 is used to create a pressure differential that is measured using pressure sensor(s) 532. Temperature and absolute pressure are also measured using sensors 534 and 532 respectively. In this case measurement system 510 includes a water analyzer 540 that makes measurements at a blind-T location upstream of the Venturi tube. In this example, the resulting total water flow rates are used to control the amount of hydrate inhibitor to inject using MEG injection system 530 that is located downstream of the measurement system 510. As in the case of measurement system 310 in FIG. 3, measurement system 510 could be installed in various locations such as measurement systems 156, 166 and 176 in FIG. 1. Additionally, other types of devices could be used instead of a Venturi tube to generate a pressure differential across which a measurement is made. Similarly, according to some embodiments, water analyzer 540 is a water analysis sensor such as OneSubsea AquaWatcher™ Water Analysis Sensor that can detect the presence of water in multiphase and wet gas flows, and determine the salinity of that water. According to some embodiments a different type of flow meter can be used, such as an ultrasonic flow meter. Note that although the example shown in FIG. 5 the location of Venturi tube 524 and water analyzer 540 are in close proximity (e.g. less than 10 meters), in general the locations of the dP measurement and the water analysis measurement could be separated within the production system by greater distances. In some embodiments, when the distance separating the dP measurement and water analysis becomes greater the calculations can be adjusted to accommodate differences in pressure and temperature between the two locations. In some other embodiments the greater distance might be tolerated for some applications.

In some embodiments, one or more of the sensors used to implement these techniques may be installed in a subsea production system in a module retrievably connected to the subsea production system. In some examples, the sensors except those used for measuring $P_r$ and $T_r$, are included in such a retrievable module. The retrievable module may also contain at least one of the control system, the chemical injection metering valve, and the choke valve. The retrievable module may be located at the well head, in a jumper, a Pipeline End Termination (PLET), a Pipeline End Manifold (PLEM), a high-integrity pressure protection system (HIPPS), a manifold, or any other part of a subsea production system such as shown in FIG. 1.

According to some embodiments, the water flow rate information derived through the proposed techniques may be presented in a Graphical User Interface in a service facility (e.g. platform 112 in FIG. 1) to facilitate human decision making concerning the production of subsea or onshore gas wells and injection of chemicals, for example. The information may be transmitted to a central data repository and may be processed further together with other data pertaining to the production and operation of gas wells.

While the subject disclosure is described through the above embodiments, it will be understood by those of ordinary skill in the art that modification to and variation of the illustrated embodiments may be made without departing from the inventive concepts herein disclosed. Moreover, while some embodiments are described in connection with various illustrative structures, one skilled in the art will recognize that the system may be embodied using a variety of specific structures.

What is claimed is:

1. A method to determine water flow rates in a gas production system from a gas well penetrating a subterranean formation comprising:
    determining a flow rate of gas flowing past a measurement location within the gas production system;
    calculating a flow rate of condensed liquid water flowing past the measurement location that has condensed from water vapor originating from the subterranean formation based in part on the determined gas flow rate;
    measuring characteristics of water flowing in the production system from which a determination can be made as to what portion of liquid water flowing originated as water produced as a liquid by the formation; and
    combining the measured characteristics of water flowing in the production system and knowledge about water residing in the formation with the calculated flow rate of condensed liquid water to derive a flow rate of water produced as a liquid by the formation.

2. The method according to claim 1 wherein the combining further comprises determining a salinity of total liquid water flowing past the measurement location based at least in part on the measured characteristics of the water, and the knowledge about the water includes knowledge about salinity of water residing in the formation.

3. The method according to claim 2 wherein the characteristics of the water are measured in close proximity to the measurement location and the measured characteristics on which the determined salinity is based include conductivity.

4. The method according to claim 3 wherein the conductivity of water flowing past the measurement location is measured in situ using a probe located within the gas production system.

5. The method according to claim 3 wherein the measuring of characteristics includes taking and analyzing samples of liquid water at the measurement location.

6. The method according to claim 1 wherein one or more of the flow rates are mass flow rates.

7. The method according to claim 1 wherein one or more of the flow rates are volumetric flow rates.

8. The method according to claim 1 wherein the calculation of condensed liquid water flow rate is also based on a flow rate of water vapor expected to have condensed from vapor given pressure and temperature conditions in the formation and at the measurement location.

9. The method according to claim 1 wherein the calculation of condensed liquid water flow rate is used to calculate a mass ratio of condensed liquid water to gas at the measurement location.

10. The method according to claim 1 wherein the gas flow rate determination comprises:
    calculating a flow rate using differential pressure measurements; and
    adjusting the flow rate to account for the presence of condensed water, formation water and condensed oil entrained in the gas.

11. The method according to claim 10 wherein the adjusting to account for the presence of condensed water and condensed oil is based in part on a calculated Lockhart-Martinelli parameter.

12. The method according to claim 1 wherein the gas well is a subsea well and the measurement location is in a subsea location.

13. The method according to claim 1 wherein the gas well is a surface well.

14. A system configured to determine water flow rates in a gas production system from a gas well penetrating a subterranean formation comprising:
    a flow meter positioned at a measurement location within the gas production system, the flow meter configured to measure a flow rate of gas;
    a processing system configured to calculate a flow rate of condensed liquid water that has condensed from vapor originating from the subterranean formation; and
    a sensor configured to measure electromagnetic properties of the produced fluid from which salinity of total liquid water flowing past the device can be determined, the processing system further configured to combine the determined salinity of the total liquid water and knowledge about the salinity of water residing in the formation with the calculated flow rate of condensed liquid water to derive a flow rate of water produced as a liquid by the formation.

15. The system of claim 14, wherein the flow meter is a wet gas flow meter.

16. The system of claim 14, wherein the flow meter is a differential pressure device.

17. The system of claim 14, wherein the flow meter is an ultrasonic flow meter.

18. The system of claim 14, comprising a control system coupled to one or more sensors of the flow meter and the sensor, wherein the control system is configured to calculate injection rates of chemicals within the gas production system based on at least one of the flow rate of water produced as a liquid by the formation or a total flow rate of produced water.

19. The system of claim 18, wherein the control system is connected to a choke valve and/or a chemical injection metering valve, wherein the control system is configured to control the choke valve and/or the chemical injection metering valve based on at least one of the flow rate of water produced as a liquid by the formation or the total flow rate of produced water.

20. The system of claim 18, wherein the gas well is a subsea gas well, the measurement location is a subsea location, wherein the flow meter and the sensor are installed subsea in a module retrievably connected to the gas production system.

21. The system of claim 20, wherein the module contains at least one of the control system, a chemical injection metering valve, and a choke valve.

22. The system of claim 20, wherein the module is located within the gas production system at a well head, in a jumper, a pipeline end termination (PLET), a pipeline end manifold (PLEM), a high-integrity pressure protection system (HIPPS), or a manifold.

* * * * *